US011457886B2

(12) United States Patent
Neumann

(10) Patent No.: US 11,457,886 B2
(45) Date of Patent: Oct. 4, 2022

(54) FLAT PANEL X-RAY IMAGING DEVICE—TWIN FLAT DETECTOR ARCHITECTURE

(71) Applicant: SCANFLEX HEALTHCARE AB, Stockholm (SE)

(72) Inventor: Volker Neumann, Hamburg (DE)

(73) Assignee: Scanflex Healthcare AB, Stockholm (SE)

( * ) Notice: Subject to any disclaimer, the term of this patent is extended or adjusted under 35 U.S.C. 154(b) by 1515 days.

(21) Appl. No.: 15/037,741

(22) PCT Filed: Nov. 19, 2014

(86) PCT No.: PCT/SE2014/051384
§ 371 (c)(1),
(2) Date: May 19, 2016

(87) PCT Pub. No.: WO2015/076742
PCT Pub. Date: May 28, 2015

(65) Prior Publication Data
US 2016/0296187 A1 Oct. 13, 2016

Related U.S. Application Data

(60) Provisional application No. 61/906,062, filed on Nov. 19, 2013.

(51) Int. Cl.
*A61B 6/00* (2006.01)
*H05G 1/32* (2006.01)

(52) U.S. Cl.
CPC ............ *A61B 6/487* (2013.01); *A61B 6/4014* (2013.01); *A61B 6/4266* (2013.01);
(Continued)

(58) Field of Classification Search
CPC ... A61B 6/4014; A61B 6/4266; A61B 6/4405; A61B 6/4435; A61B 6/4441;
(Continued)

(56) References Cited

U.S. PATENT DOCUMENTS 5,835,557 A 11/1998 Malmstrom
5,923,721 A 7/1999 Duschka
(Continued)

FOREIGN PATENT DOCUMENTS

CN 102961157 A 3/2013

*Primary Examiner* — Mark R Gaworecki
(74) *Attorney, Agent, or Firm* — Reising Ethington P.C.

(57) ABSTRACT

A mobile digital fluoroscopy system is disclosed comprising a mobile X-ray system carrier unit, a mobile control unit and an interconnecting table. The X-ray system carrier unit comprises a kV unit, a x-control unit and a first and a second X-ray system each having a transmitter and a receiver. The respective first and second X-ray systems are configured to be mounted to a G-arm and to enable X-ray imaging in mutually intersecting planes. The mobile control unit comprises a $1^{st}$ inverter, a $2^{nd}$ inverter, a $1^{st}$ transmitter generator, a $2^{nd}$ transmitter generator and a display system. The kV unit is configured to control transmitters to emit or not to emit X-ray energy, to receive image data from the receivers and to send image data via a network connection in said cable.

10 Claims, 10 Drawing Sheets

(52) U.S. Cl.
CPC .......... *A61B 6/4405* (2013.01); *A61B 6/4435* (2013.01); *A61B 6/4441* (2013.01); *A61B 6/4482* (2013.01); *A61B 6/54* (2013.01); *A61B 6/542* (2013.01); *A61B 6/545* (2013.01); *A61B 6/56* (2013.01); *A61B 6/563* (2013.01); *H05G 1/32* (2013.01); *A61B 6/463* (2013.01); *A61B 6/467* (2013.01)

(58) Field of Classification Search
CPC ....... A61B 6/4482; A61B 6/463; A61B 6/467; A61B 6/487; A61B 6/54; A61B 6/542; A61B 6/545; A61B 6/56; A61B 6/563; H05G 1/32
See application file for complete search history.

(56) References Cited

U.S. PATENT DOCUMENTS

| | | |
|---|---|---|
| 2005/0116878 A1 | 6/2005 | Warnberg |
| 2010/0249800 A1 | 9/2010 | Kim |
| 2011/0129067 A1 | 6/2011 | Fukuwara |
| 2015/0139389 A1* | 5/2015 | Eklund .................. A61B 6/487 378/62 |

* cited by examiner

FLAT PANEL X-RAY IMAGING DEVICE—TWIN FLAT DETECTOR ARCHITECTURE

FIELD OF THE INVENTION

The present invention relates in general to a preferably mobile digital fluoroscopy system for medical applications operating with an X-ray device mounted to generate X-ray images.

More specifically, the present invention relates to a fluoroscopy system having multiple X-ray devices each provided with a flat digital X-ray detector, and oriented on different axes to provide different views of the location of interest in the patient with the ability to control the area of the patient exposed to the X-ray beam via a user interface, in particular with regards to X-ray system space available within the G-arm, X-ray system maneuverability and transmitter control voltage

BACKGROUND

In orthopedic surgery environment, there is a need for allowing full access to the operating area with total control at each step. Therefore, X-ray imaging using C-stands or G-stands comprising imaging systems is commonly used, wherein a C-stand only has one X-ray imaging device while a so-called G-stand comprises two such imaging devices, with their axes oriented at an angle to each other.

A symmetrical G-stand is generally preferable to a C-stand, since it comprises two perpendicularly mounted X-ray imaging devices, and is thereby able to provide both frontal and lateral X-ray imaging with fixed settings. The ability to simultaneously see the surgical area in both a frontal and lateral view reduces the need to move and adjust the equipment during surgery, thus reducing both surgery time and radiation dose. When the need to move the equipment is reduced, better sterility is also achieved.

The ability in a G-stand to double the surgeon's view also results in accurate positioning of implants, creating a safer and more reliable method of surgery. The X-ray devices are fixed in perpendicular relation to each other in the G-stand, but the entire G-stand can be tilted somewhat for better access and views. Or in some G-stand systems, the G-stand is somewhat rotatable about a horizontal axis perpendicular to the axes of both of the X-ray devices.

One problem with conventional X-ray system carrier units is that limited space is available within the G-arm for a surgeon to operate. This is mainly due to bulky design of transmitters/receivers and that the height of the G-arm is limited by standard door height, as a mobile X-ray system carrier may be moved from room to room. Another problem with conventional systems is that the heavy high power transmitter parts make the X-ray system carrier units heavy to maneuver in terms of ergonomics.

SUMMARY OF THE INVENTION

The general object of the invention is to provide improvements in a digital fluoroscopy system for medical applications operating with first and second X-ray imaging devices mounted on a G-stand to generate X-ray images along two mutually intersecting axes. The present invention improves the limited space available within a G-arm for a surgeon to operate by separating the functionality of transmitter and receiver parts and distributing them between the X-ray system carrier unit 1 and the mobile control unit 2a. Du to this solution additional space is available within the G-arm at the same time that ergonomics of moving the X-ray system carrier unit is improved.

A problem with conventional systems is that the value of kV needed in the scan process is not unclear in order to be as efficient scan as possible without time lost in order to calibrate the system. It is also not intuitive if there is no feedback of the kV used and how much more added kV is needed in order to have a successful scan. Another problem is connecting the complex systems without having the G-arm being too bulky or heavy or with too many cables connecting the apparatus to the control unit and displays.

One embodiment of the invention solves this narrowing the area of interest by having an overview of the regulated kV value dependent on previous output and regulating a pulse width, the result is a well regulated and controlled kV output which the user can view and adjust accordingly if needed. By having an adaption unit 120 connecting the various embodiments of the systems results in less cables being needed. In one embodiment, a mobile digital fluoroscopy system, having a mobile X-ray system carrier unit having a first and a second X-ray system each having a transmitter and a receiver, said respective first and second X-ray systems being mounted on a G-arm to enable X-ray imaging in mutually intersecting planes, the system further comprising:

a mobile control unit (200) configured to receive a control voltage value via a control interface and send said control voltage value to a a monoblock 230 configured to measure a voltage used in the system and sending said measured voltage value 291 to a kV unit 250;

a kV unit 250 configured to receive a measured voltage value from said monoblock 230, calculates a regulated voltage value based on said measured voltage value 291 and sending said regulated voltage value to inverter 240;

an inverter unit 240 configured to generate a voltage value 290 to monoblock 230 based on and corresponding to said regulated voltage value received from kV unit 250;

In one embodiment, a method according to the system described herein

In one or more embodiments, a mobile digital fluoroscopy system, having a mobile X-ray system carrier unit (1), a mobile control unit (2a) and an interconnecting cable 150, wherein said X-ray system carrier unit comprises a kV unit (712), an x-control unit 713 and a first and a second X-ray system each having a transmitter (21,23) and a receiver (22,24), said respective first and second X-ray systems configured, e.g. by being mounted on a G-arm, to enable X-ray imaging in mutually intersecting planes, wherein said control unit (2a) comprises a 1st inverter 2401, a 2nd inverter 2402, a 1st transmitter generator, a 2nd transmitter generator and a display system 130, wherein said kV unit (712) is configured to control transmitters to emit or not to emit X-ray energy, to receive image data from the receivers (22,24) and to send image data via a network connection (1505) in said cable (150), wherein control transmitters comprises sending a regulated voltage value to 1st transmitter generator 212 and 2nd transmitter generator 232.

In one or more embodiments, wherein control transmitters further comprises calculating, by said kV unit (712), a regulated voltage value;

sending a control voltage, generated based on said regulated voltage value, from said 1st transmitter generator to said a 1st inverter 2401 and from said 2nd transmitter generator to said 2nd inverter 2402;

generate voltage by said 1st inverter 2401 to said 1st transmitter 21 based on said control voltage and generate voltage by said 2nd inverter 2402 to said 2nd transmitter 23 based on said control voltage.

In one or more embodiments, wherein said control unit (2a) is configured to receive functional status data in the form of user input data value via a control interface 720 and send said functional status data to said kV unit (712);

In one or more embodiments, a method in a mobile digital fluoroscopy system, having a mobile X-ray system carrier unit (1), a mobile control unit (2a) and an interconnecting cable 150, wherein said X-ray system carrier unit comprises a kV unit (712), an x-control unit 713 and a first and a second X-ray system each having a transmitter (21,23) and a receiver (22,24), said respective first and second X-ray systems being mounted on a G-arm to enable X-ray imaging in mutually intersecting planes, wherein said control unit (2a) comprises a 1st inverter 2401, a 2nd inverter 2402, a 1st transmitter generator, a 2nd transmitter generator and a display system 130, the method comprising:

controlling transmitters to emit or not to emit X-ray energy to receive image data from the receivers (22, 24);

to send image data via a network connection (1505) in said cable (150), wherein control transmitters comprises sending a regulated voltage value to 1st transmitter generator 212 and 2nd transmitter generator 232.

In one or more embodiments, wherein control transmitters further comprises:

calculating, by said kV unit (712), a regulated voltage value;

sending a control voltage, generated based on said regulated voltage value, from said 1st transmitter generator to said a 1st inverter 2401 and from said 2nd transmitter generator to said 2nd inverter 2402;

generate voltage by said 1st inverter 2401 to said 1st transmitter 21 based on said control voltage and generate voltage by said 2nd inverter 2402 to said 2nd transmitter 23 based on said control voltage.

In one embodiment, a computer program product comprising computer readable code configured to, when executed in a processor, perform any or all of the method steps described herein.

In one embodiment, a non-transitory computer readable memory on which is stored computer readable code configured to, when executed in a processor, perform any or all of the method steps described herein

BRIEF DESCRIPTION OF THE DRAWINGS

The present invention will be further explained below with reference to the accompanying drawings, in which.

DETAILED DESCRIPTION OF THE INVENTION

System Overview

Figure 1A:
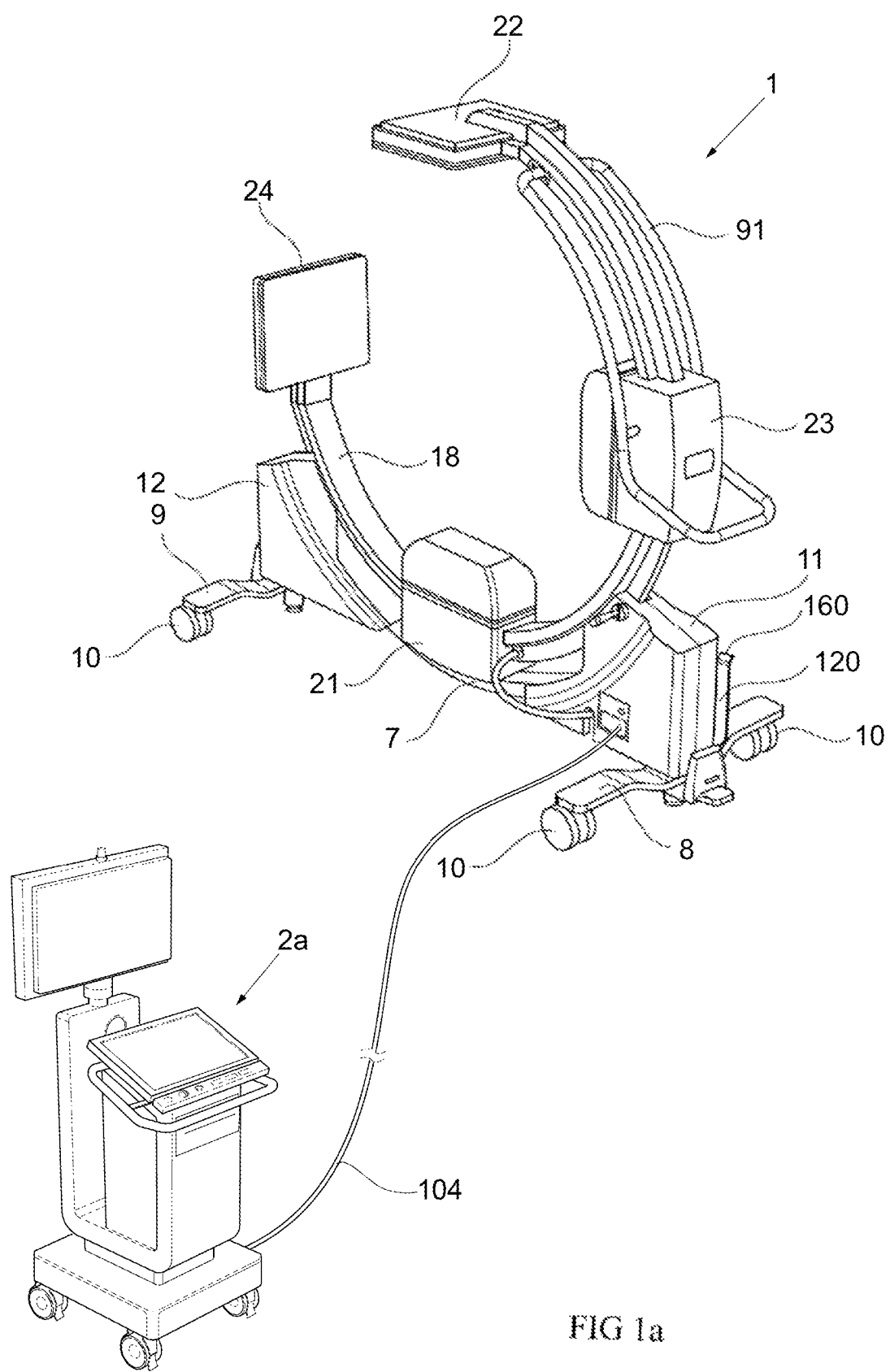
FIG. 1*a* and FIG. 1*b* shows a schematic overview of an exemplifying system embodiments of the invention in a digital fluoroscopy system configured on a G-arm on a mobile G-stand coupled to a mobile control unit.

The present invention concerns an X-ray apparatus configured as a system of components illustrated in the Figures of the drawings, adapted for use in connection with surgical orthopedic operations.

Embodiments of the invention comprise a mobile G-arm fluoroscopy system provided with flat digital X-ray detectors.

According to an embodiment, there is provided a mobile digital fluoroscopy system, comprising a mobile unit 1, also called a mobile X-ray system carrier unit 1, having a stand having a G-arm 18 suspended on a chassis frame 7; a first X-ray device 19 mounted on the G-arm 18 to transmit an X-ray beam along a first plane P1, the first X-ray device 19 having a first receiver 22 mounted on the G-arm 18 and a first transmitter 21 mounted on the G-arm 18 opposite said first receiver 22; a second X-ray device 20 mounted on the G-arm 18 to transmit an X-ray beam along a second plane P2 intersecting the first axis P1 of the first X-ray device, the second X-ray device 20 having a second receiver 24 mounted on the G-arm 18 and a second transmitter 23 mounted on the arm 18 opposite said second receiver 24, wherein said first and second receivers 22 and 24 are flat digital X-ray detectors mounted at respective ends of the G-arm.

Figure 1B:
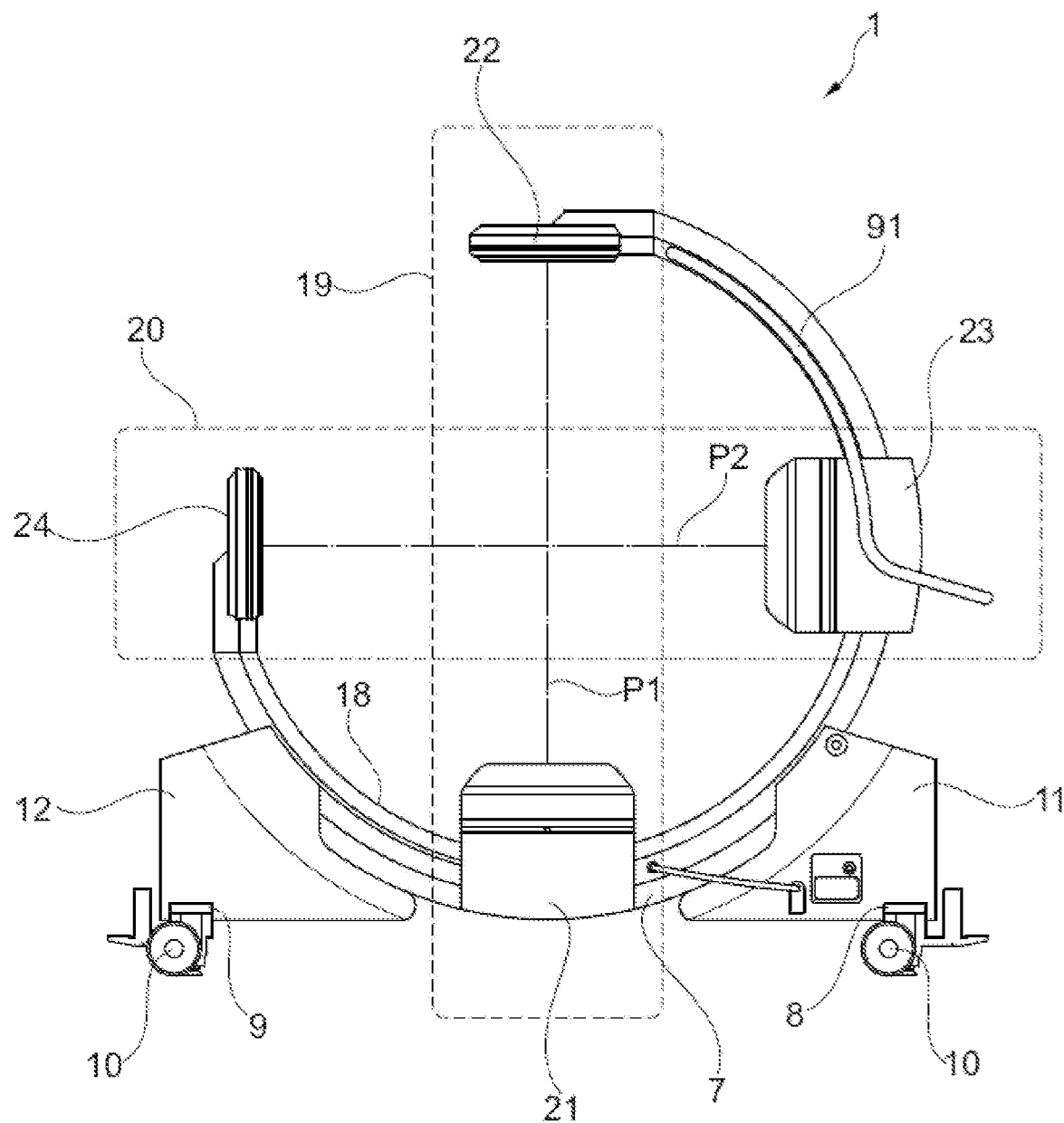

The apparatus shown in FIG. 1*a* and FIG. 1*b* comprises a mobile unit 1, i.e. a mobile X-ray system carrier unit 1 provided with two X-ray systems 19, 20 mounted to operate and transmit X-ray beams along mutually intersecting axes P1, P2. The arm 18 of the embodiment illustrated in FIG. 1*a* and FIG. 1*b* is referred to as a G-arm.

An object, typically the body of a patient undergoing surgery, is placed inside the mobile unit 1 so that beam axis P1 and beam axis P2 of the two X-ray systems cross within the object. The first X-ray device 19 includes a first transmitter 21 (an X-ray tube or x-tube) for emitting X-rays and a first receiver 22 (e.g. image intensifier or semiconductor sensors) for receiving X-rays emitted by the first transmitter 21 and having passed through the object. The first transmitter 21 may be located down below on the arm 18 and the first receiver 22 at the top of the arm 18. The second X-ray device 20 includes a second transmitter 23 (an X-ray tube or x-tube) for emitting X-rays and a second receiver 24 (e.g. image intensifier or semiconductor sensors) for receiving X-rays emitted by the second transmitter 23 and having passed through said object. The receivers 22, 24 may each comprise image intensifying means and an image capturing device, typically a CCD camera, for converting X-rays into a visible image.

FIG. 1*a* and FIG. 1*b* shows a G-arm to be placed around the patient together with a separate console 2a which can be operated by the surgeon prior to the operation or during the operation by an assistant who does not have sterility restraints. High definition monitors 4a face the surgeon displaying the X-ray images in two different orthogonal planes either in real time or in so called "cine" replay to review exactly how and precisely where a prosthetic joint component has been placed without the necessity of exposing the patient and surgeon to ore X-ray radiation.

Figure 2:
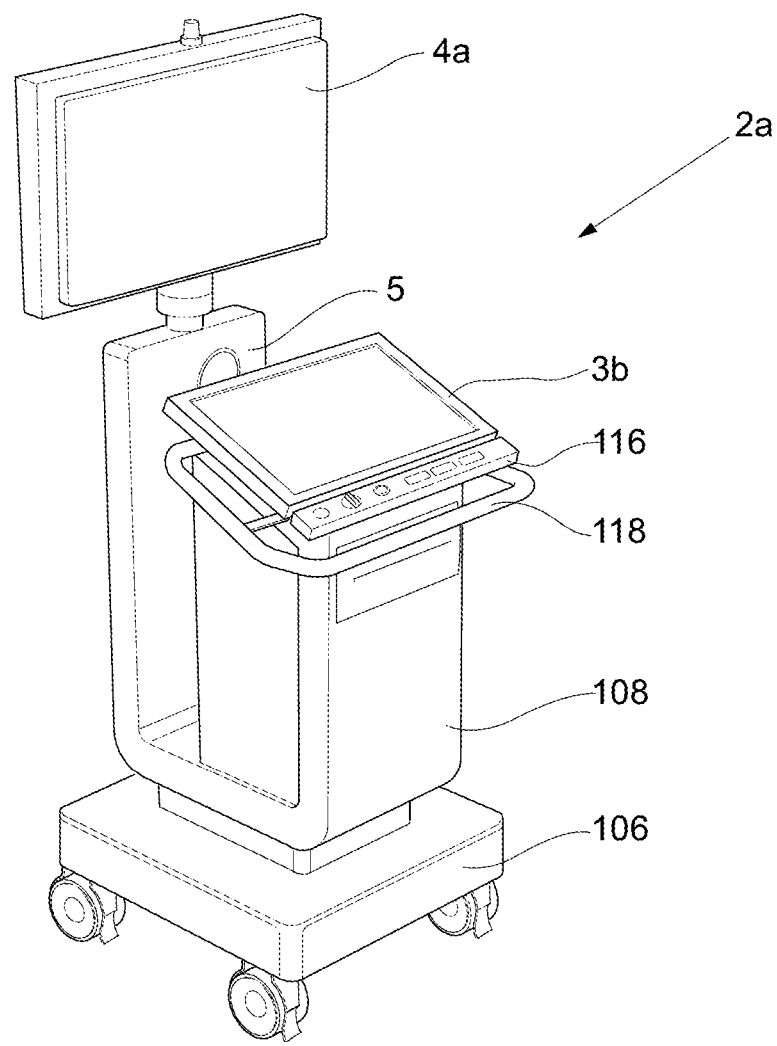
FIG. 2 shows a schematic view of an exemplifying embodiment of a mobile control unit.

FIG. 2 shows an embodiment of a mobile control unit 2a, also called console 2a, is provided with a base module 106 on wheels, a pulpit stand module 108 having a larger main part and a back part with a slot 5 in between. An operator control interface in the form of a touch screen 3b devised for presentation of one or more graphical user interfaces and a physical button panel 116 are mounted on the main part of the pulpit stand module to form a lectern like control panel, in this example also comprising a handle 118 configured for gripping when moving around the console and for resting to support ergonomic operation of the control interface. The back part of the pulpit stand module is configured for mounting display monitors or screens for presenting X-ray images.

The HD display monitors 4b can be turned to face the operator of the console or can be turned to face a different direction. During an operation, the high definition monitors will typically be turned around to present the fluoroscopic images to the surgeon. The cables 104 connecting the G-stand to the console can be wound up and stored in the slot 5 when the console and the G-stand are close to each other. The console shown in FIG. 2 has a touch screen graphic user interface (GUI) 3b, comprising in this case two fields which can be configured in various ways. The GUI may be presented with a configuration in which the left half of the touchscreen has a keyboard for inputting and recording information to identify patient or operation information for example and "cine" recordings.

Such a system may in addition to comprising high resolution monitors for presenting images to a surgeon for example also comprise components such as a foot switch (not shown) to enable the surgeon with sterile hands to switch between images taken in the respective planes. The control unit preferably further comprises at least one touch screen display for displaying image data, a control panel, and a data processor comprising image processing means adapted to receive images transmitted from said image capturing devices comprised in said receivers 22, 24. The mobile unit 1a and the control unit 2a are communicatively coupled to each other, for instance by means of a cable or through wireless signal transmission.

The control unit is further configured to receive user indications via said touch screen as user input data in the form of user input data signals, to process user input data to control data indicative of a desired adjustments of functions in system, to send said control data as control signals to such functions, to receive functional status data as status control signals from a respective functions, to process function status data to a visual representation of said function status data and to send said visual representation to said touch screen as a display signal, wherein said touch screen is configured to display said visual representation to a user.

The control unit further comprises a processor/processing unit provided with specifically designed programming or program code portions configured to control the processing unit to perform the steps and functions of embodiments of the inventive method described herein. The control unit further comprises at least one memory configured to store data values or parameters received from a processor or to retrieve and send data values or parameters to a processor. The control unit further comprises a communications interface configured to send or receive data values or parameters to/from a processor to/from external units via the communications interface.

In one or more embodiments the processor/processing unit may be a processor such as a general or specific purpose processor/processing unit for example a microprocessor, microcontroller or other control logic that comprises sections of code or code portions, stored on a computer readable storage medium, such as a memory, that are fixed to perform certain tasks but also other alterable sections of code, stored on a computer readable storage medium, that can be altered during use. Such alterable sections of code can comprise parameters that are to be used as input for the various tasks, such as receiving user indications.

In one or more embodiments the control unit further comprises a display configured to receive a display signal from a processor and to display the received signal as a displayed image, e.g. to a user control.

In one or more embodiments, the control unit further comprises an input device, e.g. integrated in the touch screen, configured to receive input or indications from a user as user input data.

In one or more embodiments, wherein communications interface may include at least one of a Local Area Network (LAN), Metropolitan Area Network (MAN), Global System for Mobile Network (GSM), Enhanced Data GSM Environment (EDGE), High Speed Downlink Packet Access (HSDPA), Wideband Code Division Multiple Access (W-CDMA), Code Division Multiple Access (CDMA), Time Division Multiple Access (TDMA), Bluetooth®, Zigbee®, Wi-Fi, Voice over Internet Protocol (VoIP), LTE Advanced, IEEE802.16m, WirelessMAN-Advanced, Evolved High-Speed Packet Access (HSPA+), 3GPP Long Term Evolution (LTE), Mobile WiMAX (IEEE 802.16e), Ultra Mobile Broadband (UMB) (formerly Evolution-Data Optimized (EV-DO) Rev. C), Fast Low-latency Access with Seamless Handoff Orthogonal Frequency Division Multiplexing (Flash-OFDM), High Capacity Spatial Division Multiple Access (iBurst®) and Mobile Broadband Wireless Access (MBWA) (IEEE 802.20) systems, High Performance Radio Metropolitan Area Network (HIPERMAN), Beam-Division Multiple Access (BDMA), World Interoperability for Microwave Access (Wi-MAX), infrared communications and ultrasonic communication, etc., but is not limited thereto.

In one or more embodiments, the processor/processing unit is communicatively coupled and communicates with a memory where data and parameters are kept ready for use by the processing unit. The one or more memories may comprise a selection of a hard RAM, disk drive, a floppy disk drive, a magnetic tape drive, an optical disk drive, a CD or DVD drive (R or RW), or other removable or fixed media drive.

In one or more embodiments, wherein communications interface 1040 may include at least one of a Local Area Network (LAN), Metropolitan Area Network (MAN), Global System for Mobile Network (GSM), Enhanced Data GSM Environment (EDGE), High Speed Downlink Packet Access (HSDPA), Wideband Code Division Multiple Access (W-CDMA), Code Division Multiple Access (CDMA), Time Division Multiple Access (TDMA), Bluetooth®, Zigbee®, Wi-Fi, Voice over Internet Protocol (VoIP), LTE Advanced, IEEE802.16m, WirelessMAN-Advanced, Evolved High-Speed Packet Access (HSPA+), 3GPP Long Term Evolution (LTE), Mobile WiMAX (IEEE 802.16e), Ultra Mobile Broadband (UMB) (formerly Evolution-Data Optimized (EV-DO) Rev. C), Fast Low-latency Access with Seamless Handoff Orthogonal Frequency Division Multiplexing (Flash-OFDM), High Capacity Spatial Division Multiple Access (iBurst®) and Mobile Broadband Wireless Access (MBWA) (IEEE 802.20) systems, High Performance Radio Metropolitan Area Network (HIPERMAN), Beam-Division Multiple Access (BDMA), World Interoperability for Microwave Access (Wi-MAX), infrared communications and ultrasonic communication, etc., but is not limited thereto.

In one or more embodiments, the processor/processing unit 1010 is communicatively coupled and communicates with a memory 1030 where data and parameters are kept ready for use by the processing unit. The one or more memories may comprise a selection of a hard RAM, disk drive, a floppy disk drive, a magnetic tape drive, an optical disk drive, a CD or DVD drive (R or RW), or other removable or fixed media drive.

Embodiments and Features of the Invention

Figure 3:
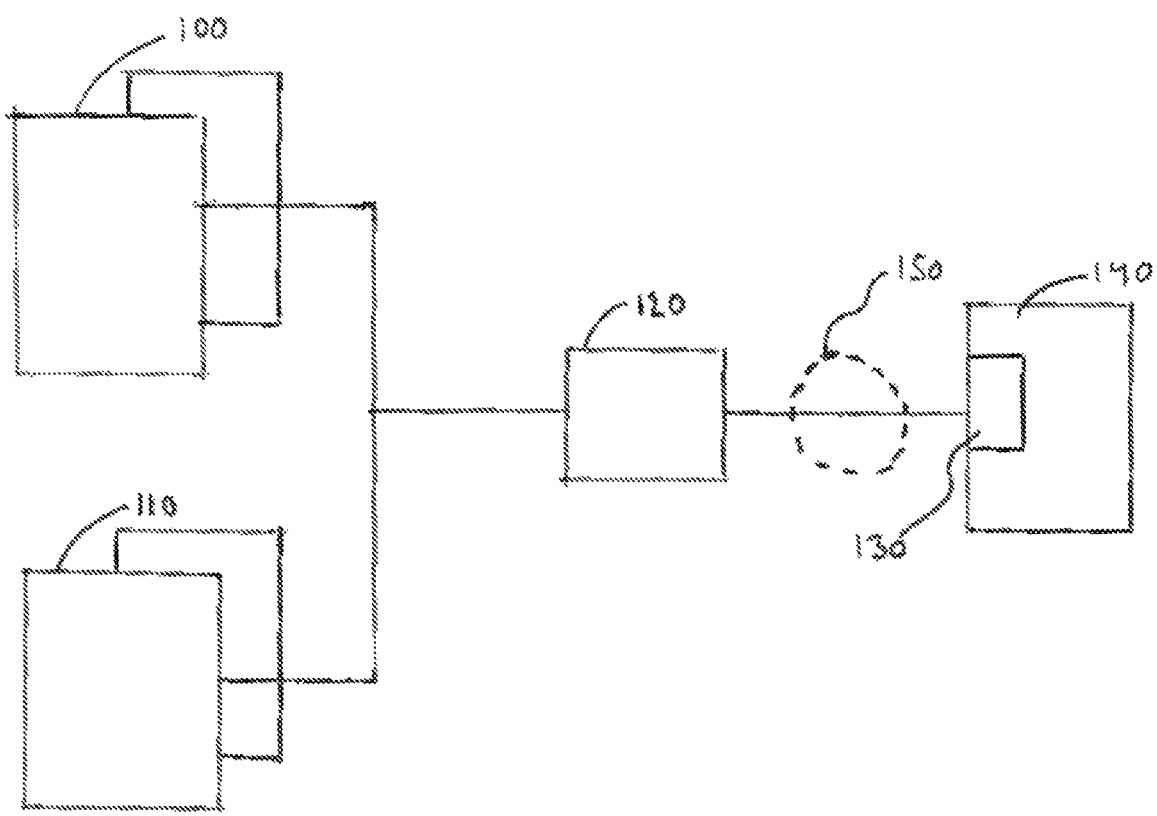
FIG. 3 shows a block diagram of a twin image detection system.

FIG. 3 shows a schematic block diagram of an architecture for synchronizing a fluoroscopy system with two x-ray systems each having a transmitter and a receiver. Said x-ray systems being attached to a mobile unit 1 or a mobile X-ray system carrier unit 1, wherein said x-ray systems are connected to control unit 140, such as the control unit/console 2*a*, through at least one cable 150.

In one embodiment said control unit 140 comprising an graphical user interface (GUI), In an alternative embodiment, the control unit may be implemented by a computing device such as a PC that may encompass the functions of said control unit 140 specially adapted for performing the steps of methods of the present disclosure, or encompass a general processor/processing unit 910 according to the description herein.

In one embodiment Control unit 140 system further comprises at least one display, that can be rotated around its foot axis, and displays scan images, e.g. to operator of the control unit, G-arm and the persons operating on the patient wherein scan images is zero or more x-ray images generated by the x-ray system. Said control unit 140 further comprises a control interface 720, e.g. a touch screen, keyboard, mouse or other devices with ability to interact with a user.

In one embodiment said control unit 140 comprises and is connected to an image acquisition and display system card 130. Said image acquisition and display system card 130 is connected to adaption unit 120 comprising panel video interface and decoder and configured to receive/send and decode/encode video, Ethernet-interface adapted to communicate data via an Ethernet network and panel control interface configured to receive user input. Said adaption unit 120 is connected to said x-ray systems comprising flat detectors 100 and image intensifiers 110.

Said image intensifiers 110 are configured to convert x-ray radiation into information e.g. displaying visible x-ray image of the scanned area. Furthermore image intensifiers can comprise a camera that converts data into pixel values.

Figure 4:
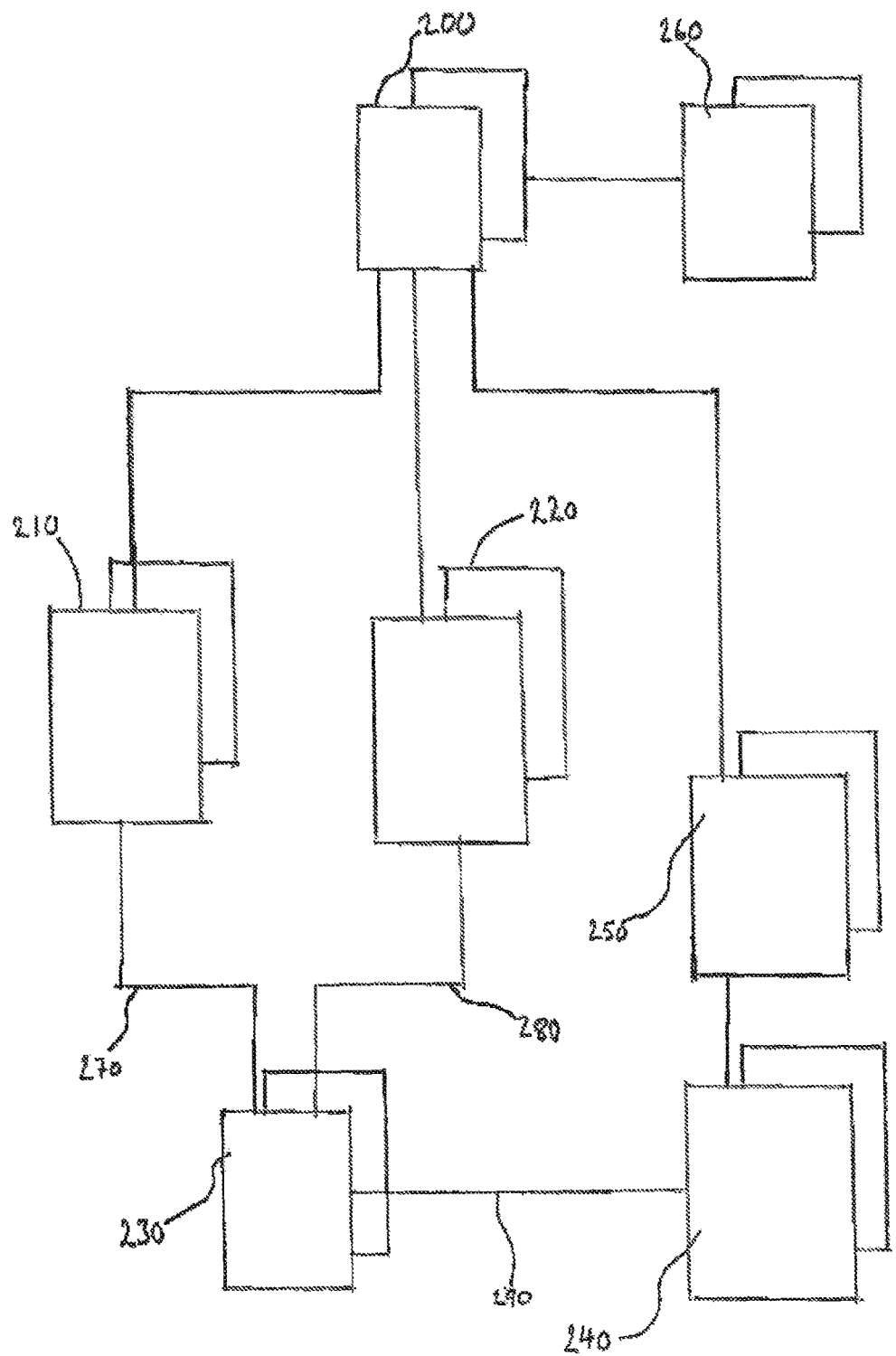
FIG. 4 shows a block diagram of a system architecture.

FIG. 4 shows a schematic view of an embodiment of a system architecture of the invention. Said architecture comprises a mobile control unit 200 connected to an input and output interface (I/O control interface) 260,720 wherein said interface 260,720 is operated whenever I/O is used in the mobile control unit 200.

Furthermore mobile control unit 200 receives functional status data in the form of user input data as user input indicative of a control voltage value at said control display unit and sends said control voltage value to a kV unit 250.

Said mobile control unit 200 is further connected to a rotor unit 220, in the transmitter for the x-ray system, for x-ray tube rotation and also connected to transmitter (21,23) also referred to as monoblock 230.

Said monoblock 230 measures voltage used in the system and sends a measured voltage value 291 to kV unit 250 wherein kV unit 250 calculates a regulated voltage value based on said measured voltage value 291 and sends said regulated voltage value to inverter 240 wherein inverter 240 generates a voltage value 290 to monoblock 230 based on and corresponding to said regulated voltage value received from kV unit 250. In one non-limiting example, the kV unit calculates a regulated voltage value by performing a look-up operation in a predefined look-up table based on said measured voltage value 291 to obtain a regulated voltage value. In one non-limiting example, the kV unit calculates a regulated voltage value by determining an image quality value based on image intensity and perform a look-up operation in a predefined look-up table based on said image quality value 291 to obtain a regulated voltage value.

Monoblock 230 sends a voltage value 270, that is calculated to a mili-ampere (mA) value by methods of milliampere (mA) sensing methods, to mA unit 210. Said mA unit 210 sends said calculated mA value to said mobile control unit 200. In one non-limiting example, the mA unit 210 calculates a mA value by performing a look-up operation in a predefined look-up table based on said voltage value 270, to obtain a mA value.

In one or more embodiments, a mobile digital fluoroscopy system, having a mobile X-ray system carrier unit having a first and a second X-ray system each having a transmitter and a receiver, said respective first and second X-ray systems being mounted on a G-arm to enable X-ray imaging in mutually intersecting planes, the system further comprising:
a mobile control unit (200) configured to receive a control voltage value via a control interface and send said control voltage value to a kV unit 250;
a monoblock 230 configured to measuring a measured voltage value 291 indicative of voltage used in the system and sending said measured voltage value 291 to a kV unit 250;
a kV unit 250 configured to receive a measured voltage value from said monoblock 230, calculates a regulated voltage value based on said measured voltage value 291 and control voltage value and sending said regulated voltage value to an inverter 240;
an inverter unit 240 configured to generate a voltage value 290 to monoblock 230 based on and corresponding to said regulated voltage value received from kV unit 250;

In one or more embodiments, a method in a mobile digital fluoroscopy system, having a mobile X-ray system carrier unit (1) having a first and a second X-ray system each having a transmitter (21, 23) and a receiver (22,24), said respective first and second X-ray systems being mounted on a G-arm to enable X-ray imaging in mutually intersecting planes, the method comprising:
receiving a control voltage value via a control interface, by a mobile control unit (200),
sending, a mobile control unit (200), said control voltage value to a kV unit 250
measuring, by a monoblock 230, a measured voltage value 291 used in the system;
calculating, by a kV unit 250, a regulated voltage value based on said measured voltage value 291 and said control voltage value
generate, by an inverter unit 240, a voltage value 290 to monoblock 230 based on and corresponding to said regulated voltage value received from kV unit 250; Use case scenarios can be the user at the control unit inputting an estimated kV value. Estimated kV value might not be a high enough value for emitted radiation to scan the patient deep enough in order to get a clear view of area of interest. Mobile control unit uses methods by calculation and regulation to calculate how much more kV the system needs in order to successfully scan the area of interest. This works as well if the kV is too high, the regulation then send a regulated kV value for the system to compensate for. The regulated kV value can be zero as well. This is especially good for the one operating the control unit as the user can view a displayed value at the control unit as well the last image scanned and the system displaying the regulation needed. This unnecessary time to calibrate kV in order to scan the area of interest is thus eliminated.

One problem with conventional X-ray system carrier units is that limited space is available within the G-arm for a surgeon to operate. This is mainly due to bulky design of transmitters/receivers and that the height of the G-arm is limited by standard door height, as a mobile X-ray system carrier may be moved from room to room. Another problem with conventional systems is that the heavy high power transmitter parts make the X-ray system carrier units heavy to maneuver in terms of ergonomics.

The present invention solves this by separating the functionality of transmitter and receiver parts and distributing them between the X-ray system carrier unit 1 and the mobile control unit 2a. Du to this solution additional space is available within the G-arm at the same time that ergonomics of moving the X-ray system carrier unit is improved.

Figure 5:
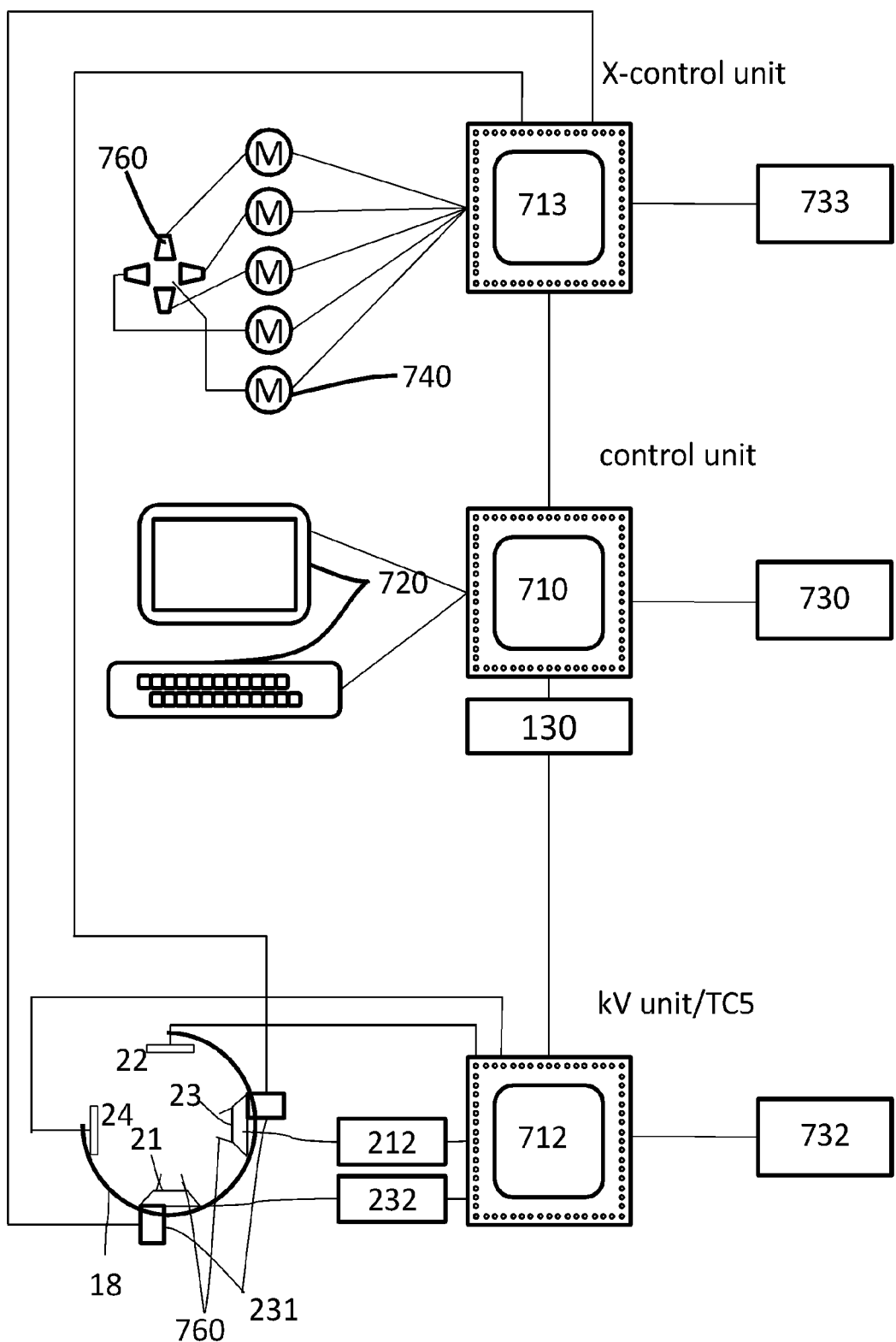
FIG. 5 shows a block diagram of another embodiment of a system architecture.
Figure 6:
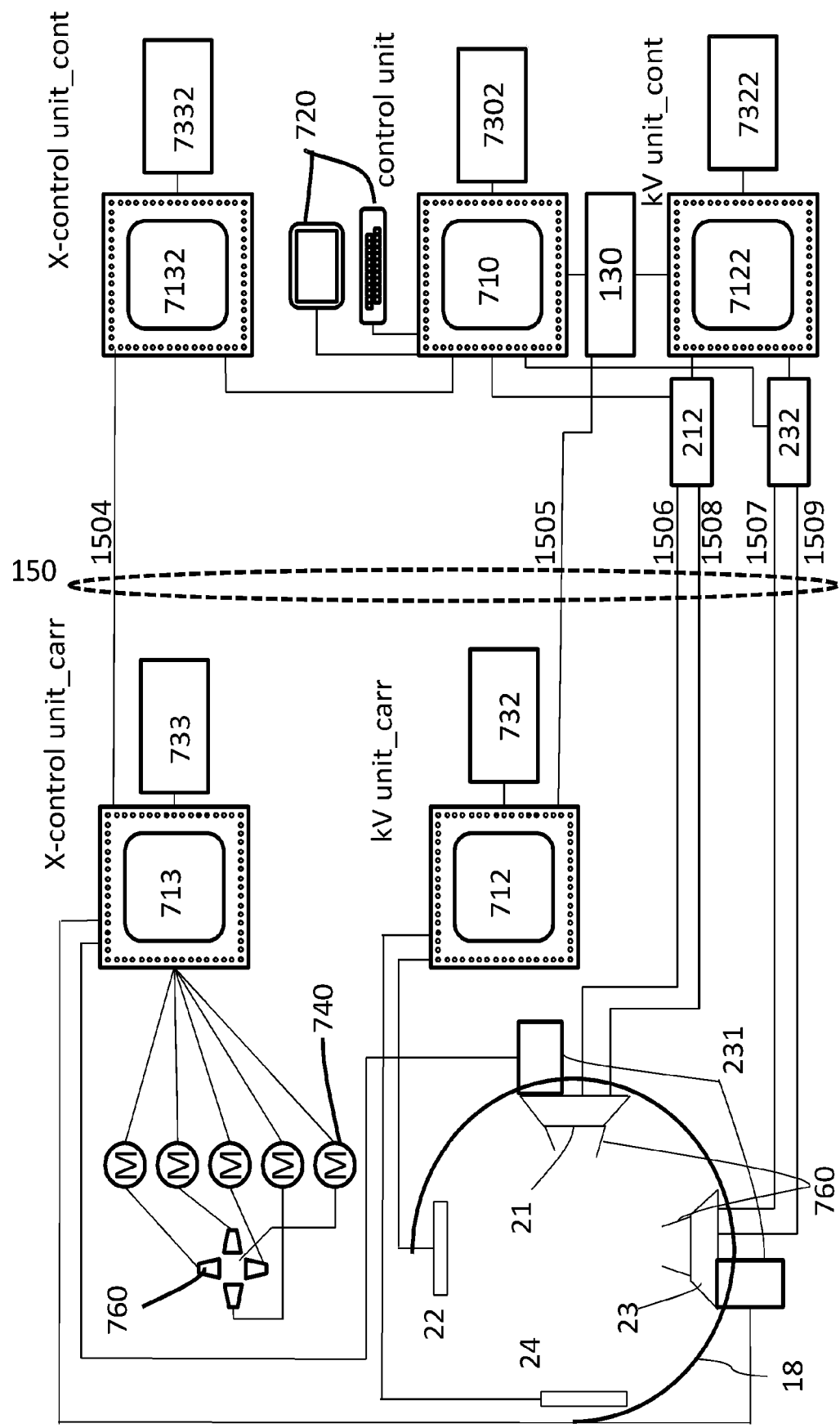
FIG. 6 shows a block diagram of another embodiment of a system architecture.

FIG. 5 shows a schematic view of an embodiment of a system architecture of the invention, wherein the system comprises a control unit 2a, 140, 200, 710 710, a kV unit 712, and an x-control unit 713. The X-ray beam transmitter is controlled by a kV unit 712 comprised at the X-ray system carrier unit 1. In one embodiment, the kV unit is configured to determine the X-ray energy to be emitted by the transmitter at a particular time and to control transmitters to emit/not to emit said determined X-ray energy based on predefined data parameters retrieved from a memory 732 communicatively coupled to said kV unit and functional status data in the form of user input data received from said control unit 2a, 140,200,710. In one embodiment, the kV unit is further configured to send third control data indicative of X-ray beam transmission to said control unit 2a, 140, 200, 710. In one embodiment, the kV unit 712 further configured to read out or receive image data from the receivers (22, 24) and send image data via a network connection 1505, e.g. Ethernet, in a cable 150 to the control unit 2a, 140,200,710. The kV unit 712 further determines the X-ray beam dose administered to an object, e.g. a patient, based on image data retrieved from the receivers, e.g. by determining an image quality measure/value based on the image intensity, as would be understood by a skilled person. In one embodiment the kV unit 712 is further configured to calculate a regulated voltage value by determining an image quality value based on image intensity an perform a look-up operation in a predefined look-up table based on said image quality value 291 to obtain a regulated voltage value. In one embodiment, the kV unit is further configured to send functional status data indicative of the determined X-ray beam dose to said control unit 2a, 140,200,710 and to determine the X-ray beam dose administered to an object, e.g. a patient. The kV unit 712, the transmitters (21, 23), the receivers (22,24), the memory 732 and the control unit 2a, 140,200,710 are communicatively coupled to each other, for instance by means of a cable or through wireless signal transmission. The area of interest or area radiated by the X-ray beam may be controlled by narrowing the X-ray beam by the use of collimator plates 760 disposed between a beam transmitter and a beam receiver. The control of the area of interest is achieved by the use of a x-control unit 713 configured or adapted to receive functional status data as control data in the form of control signals from said control unit 2a, 140,200,710, wherein the control data is based on processed user input data, to control servo motors 740 to a predetermined position based on said control data by sending servo motor signals, thereby narrowing the area of interest of the patient exposed to the X-ray beam. In one embodiment, the x-control unit 713 is further configured to obtain dose area product (DAP) measurement values from a DAP chamber 231, also referred to as ionization chamber. Dose area product (DAP) is a quantity used in assessing the radiation risk from diagnostic x-ray examinations and interventional procedures. It is defined as the absorbed dose multiplied by the area irradiated, typically expressed in gray square centimeters ($Gy*cm^2$), $mGy*cm^2$ or $cGy*cm^2$. Examples of DAP measurement values are cumulative dose, DAP dose and entrance dose. Functional status data indicative of the status of a servo motor is obtained by the x-control unit by receiving servo motor signals and to send functional status data as status control signals to said control unit 2a, 140, 200,710. In one embodiment the x-control unit is configured to receive functional status data as control signals from said control unit 2a, 140,200,710, wherein the control data is based on processed user input data, to control servo motors to a predetermined position based on said functional status data by sending servo motor signals, thereby narrowing the area of interest of the patient exposed to the X-ray beam and to obtain functional status data indicative of the status of a servo motor by receiving servo motor signals and to send functional status data as status control signals to said first control unit 2a, 140,200,710. The x-control unit 713, the DAP chambers 231, the control unit 2a, 140,200,710 and the servo motors are communicatively coupled to each other, for instance by means of a cable or through wireless signal transmission. FIG. 6 shows a schematic view of an embodiment of the invention, wherein the system comprises a control unit 2a, 140,200,710 710, a kV unit 712, a kV unit_cont 7122 communicatively coupled to a memory 7322, an x-control unit 713 and an x-control unit_cont 7132 communicatively coupled to a memory 7332. In embodiments, the kV unit 712 and the x-control unit 713 are communicatively coupled via a cable 150 to the x-control unit_cont 7132, kV unit_cont 7122 and the control unit 2a. In embodiments, the kV unit 712 is communicatively coupled via a network connection 1505, e.g. Ethernet, in the cable 150 to the kV unit_cont 7122. In embodiments, the x-control unit 713 is communicatively coupled via a connection 1505, e.g. a Controller Area Network (CAN) bus, in the cable 150 to the x-control unit_cont 7132. In embodiments, the system further comprise a $1^{st}$ transmitter generator unit 212 communicatively coupled to the kV unit cont 7122 and the control unit 2a, 140,200,710 710.

In embodiments, the $1^{st}$ transmitter generator unit 212 is further coupled to the $1^{st}$ transmitter by transmitter high power supply, connection 1508. In embodiments, the $1^{st}$ transmitter generator unit 212 is further coupled to the $1^{st}$ transmitter by a 1506 $1^{st}$ transmitter control. In embodiments, the system further comprise a $2^{nd}$ transmitter generator unit 232 communicatively coupled to the kV unit- _cont 7122 and the control unit 2a, 140,200,710 710. In embodiments, the $2^{nd}$ transmitter generator unit 232 is further coupled to the $2^{nd}$ transmitter by transmitter high power supply, connection 1509 in cable 150. In embodiments, the $2^{nd}$ transmitter generator unit 232 is further coupled to the $2^{nd}$ transmitter by a 1507 $2^{nd}$ transmitter control connection in cable 150. The X-ray beam transmitters 21, 23 are controlled by a kV unit 712 comprised at the X-ray system carrier unit. In embodiments, the X-ray beam transmitters 21, 23 are further controlled via a kV unit_cont 7122 comprised at control unit 2a, 140,200,710. In one embodiment, the kV unit is configured to determine the X-ray energy to be emitted by the transmitter at a particular time and to control transmitters to emit/not to emit said determined X-ray energy based on predefined data parameters retrieved from a memory 732 communicatively coupled to said kV unit 712 and functional status data in the form of user input data received from said control unit 2a, 140,200,710. In one embodiment, the kV unit_cont 7122 is configured to determine the X-ray energy to be emitted by the transmitter at a particular time and to control transmitters to emit/not to emit said determined X-ray energy based on predefined data parameters retrieved from a memory 7322 communicatively coupled to said kV unit_cont 7122 and functional status data in the form of user input data received from said control unit 2a, 140,200,710. In one embodiment, the kV unit 712 is further configured to send third control data indicative of X-ray beam transmission to said control unit 2a, 140,200, 710. In one embodiment, the kV unit 712 further configured to read out or receive image data from the receivers (22,24) and send image data via a network connection 1505, e.g. Ethernet, in a cable 150 to the control unit 2a, 140,200,710. The kV unit 712 further determines the X-ray beam dose administered to an object, e.g. a patient, based on image data retrieved from the receivers, e.g. by determining an image quality measure/value based on the image intensity, as would be understood by a skilled person. In one embodiment the kV unit 712 is further configured to calculate a regulated voltage value by determining an image quality value based on image intensity an perform a look-up operation in a predefined look-up table based on said image quality value 291 to obtain a regulated voltage value. In one embodiment, the kV unit is further configured to send functional status data indicative of the determined X-ray beam dose to said control unit 2a, 140,200,710 and to determine the X-ray beam dose administered to an object, e.g. a patient. The kV unit 712, the transmitters (21, 23), the receivers (22,24), the memory 732 and the control unit 2a, 140,200,710 are communicatively coupled to each other, for instance by means of a cable or through wireless signal transmission. The area of interest or area radiated by the X-ray beam may be controlled by narrowing the X-ray beam by the use of collimator plates 760 disposed between a beam transmitter and a beam receiver. The control of the area of interest is achieved by the use of a x-control unit 713 configured or adapted to receive functional status data as control data in the form of control signals from said control unit 2a, 140,200,710, wherein the control data is based on processed user input data, to control servo motors 740 to a predetermined position based on said control data by sending servo motor signals, thereby narrowing the area of interest of the patient exposed to the X-ray beam. In one embodiment, the x-control unit 713 is further configured to obtain dose area product (DAP) measurement values from a DAP chamber 231, also referred to as ionization chamber. Dose area product (DAP) is a quantity used in assessing the radiation risk from diagnostic x-ray examinations and interventional procedures. It is defined as the absorbed dose multiplied by the area irradiated, typically expressed in gray square centimeters (Gy*cm$^2$), mGy*cm$^2$ or cGy*cm$^2$. Examples of DAP measurement values are cumulative dose, DAP dose and entrance dose. Functional status data indicative of the status of a servo motor is obtained by the x-control unit by receiving servo motor signals and to send functional status data as status control signals to said control unit 2a, 140,200,710. In one embodiment the x-control unit is configured to receive functional status data as control signals from said control unit 2a, 140,200,710, wherein the control data is based on processed user input data, to control servo motors to a predetermined position based on said functional status data by sending servo motor signals, thereby narrowing the area of interest of the patient exposed to the X-ray beam and to obtain functional status data indicative of the status of a servo motor by receiving servo motor signals and to send functional status data as status control signals to said first control unit 2a, 140,200,710. The x-control unit 713, the DAP chambers 231, the control unit 2a, 140,200,710 and the servo motors are communicatively coupled to each other, for instance by means of a cable or through wireless signal transmission.

Figure 7:
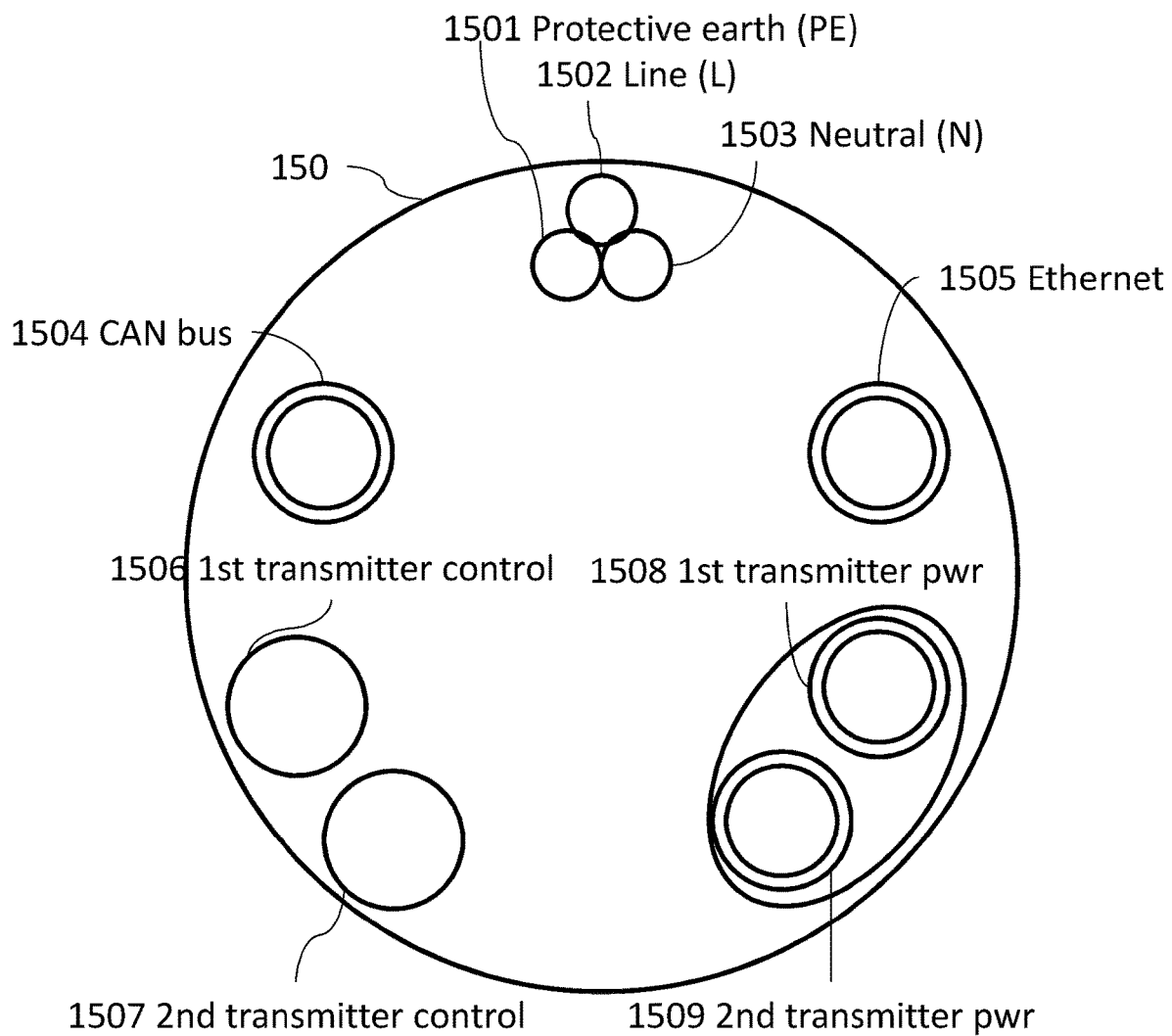
FIG. 7 shows an embodiment of a cable connecting the control unit 2a with the X-ray system unit (1).
Figure 8:
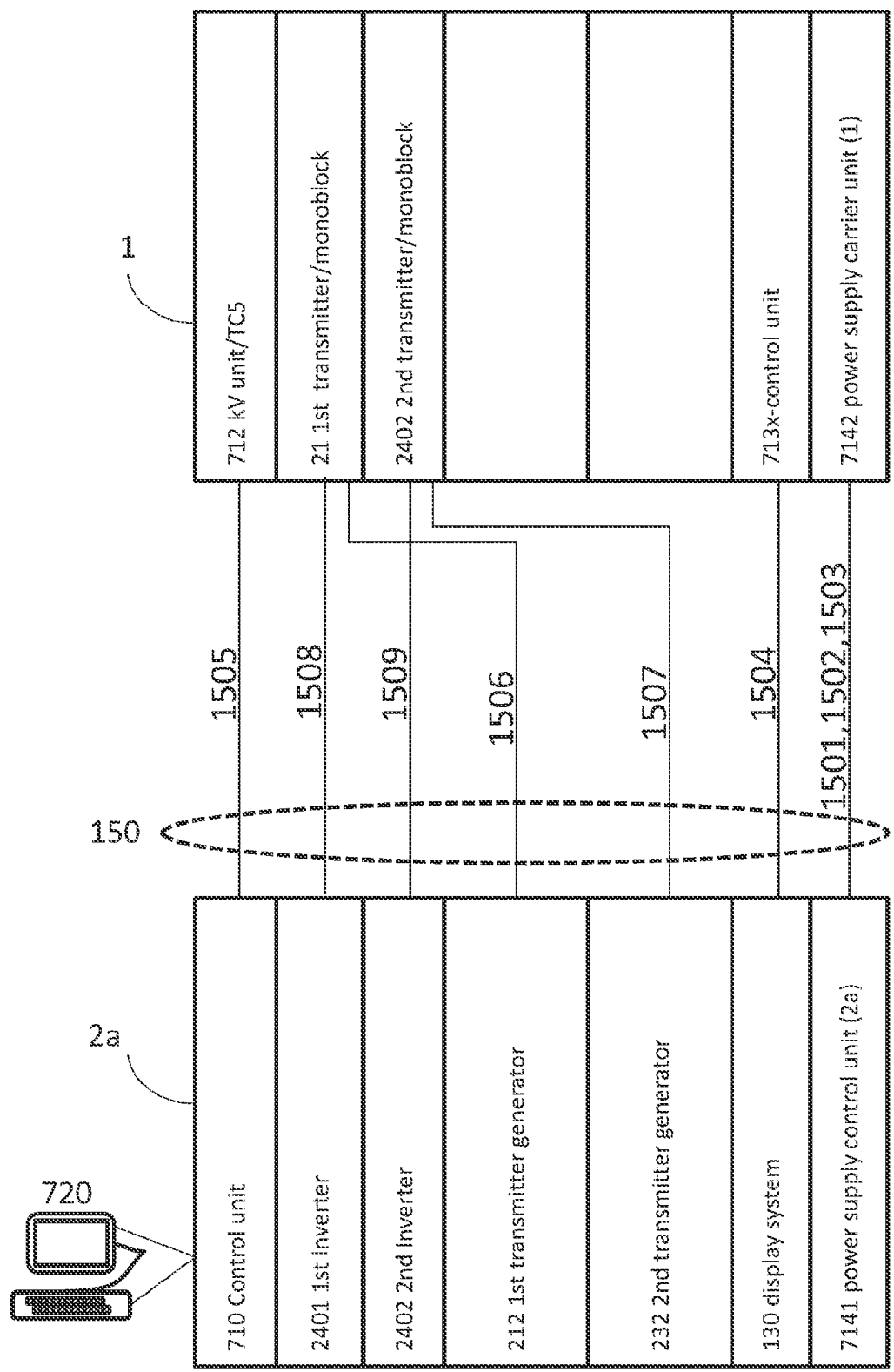
FIG. 8 shows yet an embodiment system comprising a cable connecting the control unit 2a with the X-ray system unit (1).

FIG. 7 shows a schematic view of an embodiment of a cable 150 connecting the X-ray system carrier unit 1 with the control unit 2a, 140, 200, 710. The cable 150 comprise mains-connections 1501 protective earth (PE), 1502 line (L) and 1503 neutral (N), 1504 CAN bus, 1505 Ethernet, 1506 $1^{st}$ transmitter control, 1507 $2^{nd}$ transmitter control, 1508 $1^{st}$ transmitter high power supply and 1509 $2^{nd}$ transmitter high power supply. The mains-connections 1501 protective earth (PE), 1502 line (L) and 1503 neutral (N) provides main power supply from X-ray system carrier unit 1 to the control unit 2a, 140,200,710 or vice versa. The 1504 CAN bus connects the x-control unit 713 to the control unit 2a, 140,200,710 directly or via the display system card 130 and transfers functional status data in both directions, e.g. indicative of captured X-ray images, target power of the transmitters (21, 23) in kV or mA values and activation timing of the transmitters. The 1506 $1^{st}$ transmitter control connects the first transmitter to a transmitter generator unit and transfers functional status data in both directions, e.g. indicative of detected errors. The 1507 $2^{nd}$ transmitter control connects the second transmitter to a transmitter generator unit and transfers functional status data in both directions, e.g. indicative of detected errors. The 1508 $1^{st}$ transmitter high power supply connects the first transmitter 21 to a first inverter unit and transfers high power to the first transmitter 21 or monoblock. The 1509 $2^{nd}$ transmitter high power supply connects the second transmitter 23 to a second inverter unit and transfers high power to the second transmitter 23 or monoblock. FIG. 8 shows another schematic view of an embodiment of a cable 150 connecting the X-ray system carrier unit 1 with the control unit 2a, 140,200,710. The mains-connections 1501 protective earth (PE), 1502 line (L) and 1503 neutral (N) provides power from X-ray system carrier unit power supply 7142 to the control unit power supply 7141 or vice versa. The 1504 CAN bus connects the x-control unit 713 to the control unit 2a, 140,200,710 directly (not shown in image) or via the display system card 130 and transfers functional status data in both directions, e.g. indicative of a predetermined position to control servo motors 740 to or DAP parameter values. The 1505 connects the kV unit/TC5 unit 712 to the control unit 2a, 140,200,710 directly or via the display system card 130 (not shown in the image) and transfers functional status data in both directions, e.g. indicative of captured X-ray images, target power of the transmitters (21,23) in kV or mA values and activation timing of the transmitters. The 1506 $1^{st}$ transmitter control connects the first transmitter 21 to a transmitter generator unit 212 and transfers functional status data in both directions, e.g. indicative of detected errors in the transmitter/monoblock. The 1507 $2^{nd}$ transmitter control connects the second transmitter 23 to a transmitter generator unit 232 and transfers functional status data in both directions, e.g. indicative of detected errors. The 1508 $1^{st}$ transmitter high power supply connects the first transmitter 21 to a first inverter unit 2401 and transfers high power to the first transmitter 21 or monoblock. The 1509 $2^{nd}$ transmitter high power supply connects the second transmitter 23 to a second inverter unit 2402 and transfers high power to the second transmitter 23 or monoblock.

Figure 9:
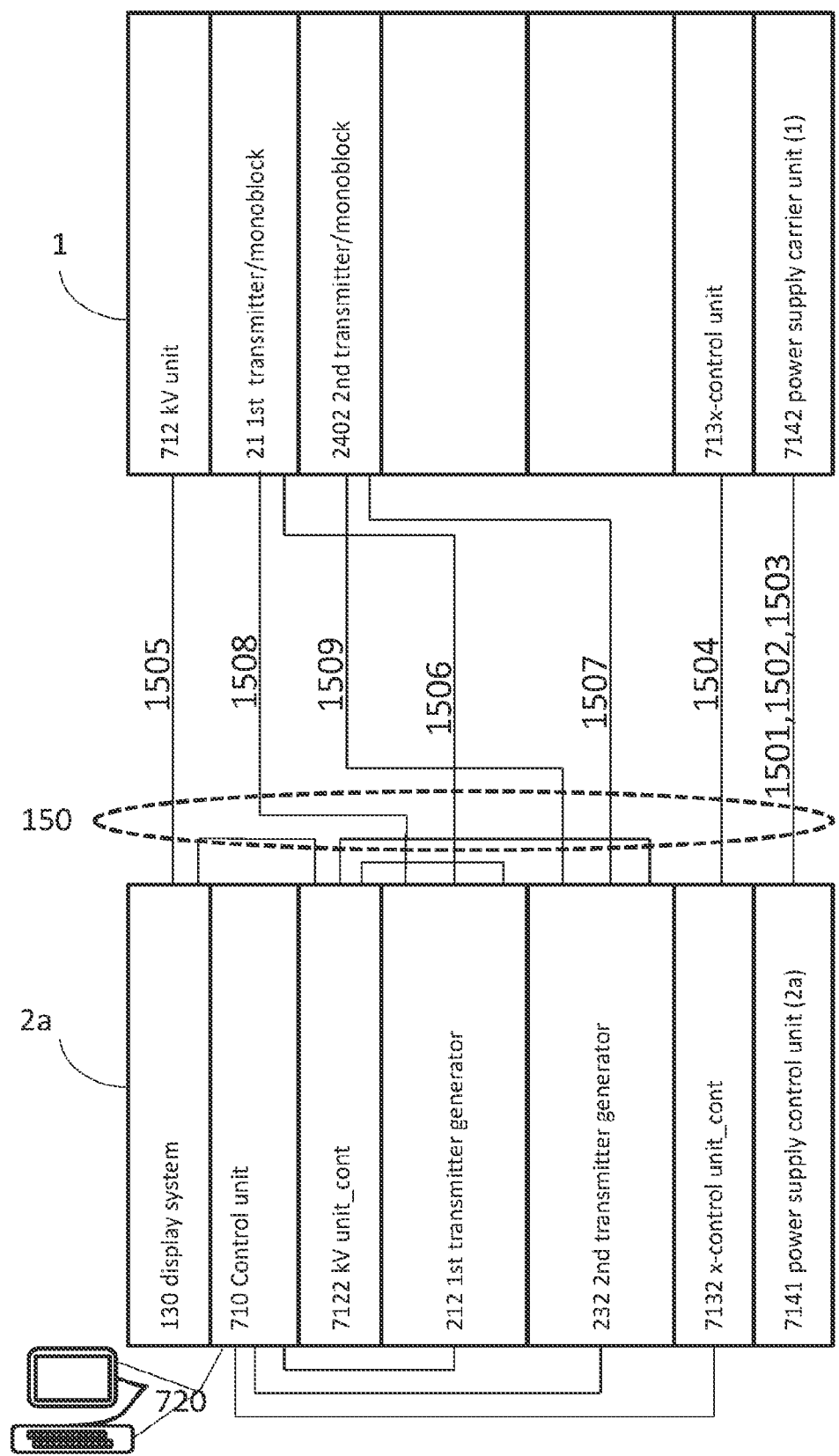
FIG. 9 shows yet an embodiment system comprising a cable connecting the control unit 2a with the X-ray system unit (1).

FIG. 9 shows another schematic view of an embodiment of a system comprising a cable 150 connecting the X-ray system carrier unit 1 with the control unit 2a, 140,200,710. The mains-connections 1501 protective earth (PE), 1502 line (L) and 1503 neutral (N) provides power from X-ray system carrier unit power supply 7142 to the control unit power supply 7141 or vice versa. The 1504 CAN bus connects the x-control unit 713 to x-control unit_cont 7132 and transfers functional status data in both directions, e.g. indicative of a predetermined position to control servo motors 740 to or DAP parameter values. The 1505 connects the kV unit 712 to the display system card 130 (not shown in the image) and transfers functional status data in both directions, e.g. indicative of captured X-ray images, target power of the transmitters (21, 23) in kV or mA values and activation timing of the transmitters. The 1506 $1^{st}$ transmitter control connects the first transmitter 21 to a $1^{st}$ transmitter generator unit 212 and transfers functional status data in both directions, e.g. indicative of detected errors in the transmitter/monoblock. The 1507 $2^{nd}$ transmitter control connects the second transmitter 23 to a transmitter generator unit 232 and transfers functional status data in both directions, e.g. indicative of detected errors. The 1508 $1^{st}$ transmitter high power supply connects the first transmitter 21 to a $1^{st}$ transmitter generator unit 212 and transfers high power to the first transmitter 21 or monoblock. The 1509 $2^{nd}$ transmitter high power supply connects the second transmitter 23 to a $2^{nd}$ transmitter generator unit 232 and transfers high power to the second transmitter 23 or monoblock. The $1^{st}$ transmitter generator unit 212 is further connected to the kV unit unit_cont 7122 and the control unit 2a, 140,200,710. The $2^{nd}$ transmitter generator unit 232 is further connected to the kV unit unit_cont 7122 and the control unit 2a, 140,200,710. In embodiments, the kV unit unit_cont 7122 is further connected to the display system 130. In embodiments, the x-control unit_cont 7132 is further communicatively connected to the control unit 2a, 140, 200, 710. In embodiments, the control unit 2a, 140,200,710 further comprises a control interface 720 configured to receive user input data as user indications from a user. In embodiments, a single kV unit unit_cont 7122 comprised in a control unit 2a, 140, 200, 710 is coupled via a 1505 Ethernet connection to multiple X-ray carrier units, each comprising a kV unit 712, thereby affectively cascading multible X-ray systems controlled by a single control unit 2a, 140, 200, 710.

One advantage of the present invention is that the volume of the X-ray devices on the X-ray carrier unit (1) is reduced by distributing functionality between the X-ray carrier unit (1) and the control unit (2a), thus leaving more room within the G-arm for a surgeon to operate.

Yet another advantage of the present invention is that the physically heavy high power parts of the system is separated from the X-ray carrier unit (1), thus making maneuverability more ergonomic, in other words easier to adjust to a new position. Thus, different types of X-ray systems or additional dimensions of the same X-ray system may be added or cascaded whilst still using the same control unit 2a, 140, 200, 710.

In one or more embodiments, a computer program product comprising computer readable code configured to, when executed in a processor, perform any or all of the method steps described herein.

In one or more embodiments, a non-transitory computer readable memory on which is stored computer readable code configured to, when executed in a processor, perform any or all of the method steps described herein.

A tangibly embodied computer-readable medium including executable code that, when 5 executed, causes a control unit to perform any or all of the method steps described herein.

A tangibly embodied computer-readable medium including executable code that, when executed, causes a servo motor unit to perform any or all of the method steps described herein.

The invention claimed is:

1. A mobile digital fluoroscopy system, having a mobile X-ray system carrier unit, a mobile control unit and an interconnecting cable, wherein said X-ray system carrier unit comprises a kV unit, an x-control unit and a first and a second X-ray system each having a transmitter and a receiver, said respective first and second X-ray systems being configured, by being mounted to a G-arm, to enable X-ray imaging in mutually intersecting planes, wherein said control unit comprises a $1^{st}$ inverter, a $2^{nd}$ inverter, a $1^{st}$ transmitter generator, a $2^{nd}$ transmitter generator and a display system, wherein said kV unit is configured to control transmitters to emit or not to emit X-ray energy, to receive image data from the receivers and to send image data via a network connection in said cable.

2. The system of claim 1, wherein said controlling of transmitters comprises sending a regulated voltage value to $1^{st}$ transmitter generator and $2^{nd}$ transmitter generator.

3. The system of claim 1, wherein control transmitters further comprise
   calculating, by said kV unit, a regulated voltage value;
   sending a control voltage, generated based on said regulated voltage value, from said $1^{st}$ transmitter generator to said a $1^{st}$ inverter and from said $2^{nd}$ transmitter generator to said $2^{nd}$ inverter;
   generate voltage by said $1^{st}$ inverter to said $1^{st}$ transmitter based on said control voltage and generate voltage by said $2^{nd}$ inverter to said $2^{nd}$ transmitter based on said control voltage.

4. The system of claim 1, wherein said control unit is configured to receive functional status data in the form of user input data value via a control interface and send said functional status data to said kV unit.

5. The system of claim 1, comprising:
   a monoblock configured to measure a voltage used in the system and sending said measured voltage value to a kV unit;
   a kV unit configured to receive a measured voltage value from said monoblock, calculates a regulated voltage value based on said measured voltage value and sending said regulated voltage value to inverter;
   an inverter unit configured to generate a voltage value to monoblock based on and corresponding to said regulated voltage value received from kV unit.

6. A computer program product comprising non-transitory computer readable code configured to, when executed in a processor, perform the functions in claim 1.

7. A non-transitory computer readable memory on which is stored computer readable code configured to, when executed in a processor, performs the functions in claim 1.

8. A method in a mobile digital fluoroscopy system, having a mobile X-ray system carrier unit having a first and a second X-ray system each having a transmitter and a receiver, said respective first and second X-ray systems being configured, mounted on a G-arm, to enable X-ray imaging in mutually intersecting planes, the method comprising:
    receiving a control voltage value via a control interface and send said control voltage value to a kV unit
    measuring a voltage used in the system;
    calculating a regulated voltage value based on said measured voltage value and said control voltage value
    generate a voltage value based on and corresponding to said regulated voltage value received from said kV unit.

9. A method in a mobile digital fluoroscopy system, having a mobile X-ray system carrier unit, a mobile control unit and an interconnecting cable, wherein said X-ray system carrier unit comprises a kV unit, an x-control unit and a first and a second X-ray system each having a transmitter and a receiver, said respective first and second X-ray systems being configured, mounted on a G-arm, to enable X-ray imaging in mutually intersecting planes, wherein said control unit comprises a $1^{st}$ inverter, a $2^{nd}$ inverter, a $1^{st}$ transmitter generator, a $2^{nd}$ transmitter generator and a display system, the method comprising:
    controlling transmitters to emit or not to emit X-ray energy
    to receive image data from the receivers;
    to send image data via a network connection in said cable, wherein controlling transmitters comprises sending a regulated voltage value to $1^{st}$ transmitter generator and 2nd transmitter generator.

10. The method of claim 9, wherein control transmitters further comprises:
    calculating, by said kV unit, a regulated voltage value;
    sending a control voltage, generated based on said regulated voltage value, from said $1^{st}$ transmitter generator to said a $1^{st}$ inverter and from said $2^{nd}$ transmitter generator to said $2^{nd}$ inverter;
    generate voltage by said $1^{st}$ inverter to said $1^{st}$ transmitter based on said control voltage and generate voltage by said $2^{nd}$ inverter to said $2^{nd}$ transmitter based on said control voltage.

\* \* \* \* \*